United States Patent [19]

Crepaldi et al.

[11] Patent Number: 5,426,120
[45] Date of Patent: Jun. 20, 1995

[54] PHARMACEUTICAL COMPOSITION CONTAINING γ-HYDROXYBUTYRIC ACID OR ITS LACTONE IN THE TREATMENT OF DRUG DEPENDENCE AND NUTRITIONAL DISORDERS

[76] Inventors: Gaetano Crepaldi, Via Palermo, 8,, I-35142 Padova; Santo Ferrara, Via Napoli, 29-Tencarola, I-35030 Selvazzano Dentro; Luigi Gallimberti, Via San Mattia, 16, I-35142 Padova; Gian L. Gessa, Vicolo XII 18 - S. Giovanni, I-09100 Cagliari, all of Italy

[21] Appl. No.: 81,388

[22] PCT Filed: Jun. 23, 1992

[86] PCT No.: PCT/EP92/01409
§ 371 Date: Jun. 29, 1993
§ 102(e) Date: Jun. 29, 1993

[87] PCT Pub. No.: WO93/00083
PCT Pub. Date: Jan. 7, 1993

[30] Foreign Application Priority Data

Jun. 28, 1991 [IT] Italy ............................ MI91A01791

[51] Int. Cl.⁶ ..................... A61K 31/19; A61K 31/34; A61K 31/045
[52] U.S. Cl. ................................... 514/473; 514/557; 514/810; 514/811; 514/812; 514/813; 514/909; 514/910
[58] Field of Search ............... 514/473, 557, 810, 811, 514/812, 813, 909, 910

[56] References Cited

FOREIGN PATENT DOCUMENTS 0344704 12/1989 European Pat. Off. .
0139519 1/1980 German Dem. Rep. .

*Primary Examiner*—Johann Richter
*Assistant Examiner*—Michael B. Hydorn
*Attorney, Agent, or Firm*—Bucknam and Archer

[57] ABSTRACT

γ-Hydroxybutyric acid and its physiologically equivalent forms are useful in the treatment of the syndromes of abstinence, craving and dependence on drugs, drugs of abuse, psychotropics, stupefacient and/or psychoactive substances, nicotine, or nutritional disorders.

9 Claims, No Drawings

PHARMACEUTICAL COMPOSITION CONTAINING γ-HYDROXYBUTYRIC ACID OR ITS LACTONE IN THE TREATMENT OF DRUG DEPENDENCE AND NUTRITIONAL DISORDERS

This application is the National stage of PCT/EP92/01409, filed 23 Jun. 1992.

The present invention relates to pharmaceutical compositions having therapeutic effects on abstinence, on craving (the intense and compulsive desire for a substance), and on dependence on drugs, drugs of abuse, psychotropics, stupefacient and/or psychoactive substances, nicotine and also on nutritional disorders (in particular bulimia, obesity and anorexia), such compositions being characterised in that they contain, as the active principle, γ-hydroxybutyric acid (GHB), or salts thereof with pharmaceutically acceptable cations, or the corresponding lactone.

The invention further relates to the use of γ-hydroxybutyric acid or of its physiologically equivalent forms for the preparation of a medicament which is useful in the treatment of the withdrawal syndrome induced by drugs, drugs of abuse, psychotropics, stupefacient and/or psychoactive substances and nicotine.

The relevant salts of GHB include, for example, alkali metal (e.g. sodium or potassium) salts, alkaline earth metal (e.g. calcium or magnesium) salts, ammonium salts, salts of pharmaceutically acceptable bases (ethanolamine, diethanolamine, piperidine, piperazine and the like), salts of basic amino acids (lysine, ornithine, citrulline) etc.

GHB, various salts thereof and its lactone have been known for decades. The acid is a normal constituent of the central nervous system (CNS) of mammals, with the highest concentration in the hypothalamus and in the basal ganglia (c % 1.78 nM/g and 4.1 nM/g in rats and in guinea pigs, respectively).

The almost universal prevalence of binding sites for GHB in the CNS makes it probable that such a compound acts as a neurotransmitter and as neuro-modulator, rather than as incidental metabolite of γ-aminobutyric acid (GABA). The use of GHB in clinical practice has been known for many years for general anaesthetic and narcoleptic purposes, with prevailing utilisation by way of intravenous administration (see Anesth. Analg. (Cleve), 41, 721–726, 1962; Science 143, 1045–1047, 1964; Electroencephalogr. Clin. Neurophysiol., 22, 558–562, 1967; Sleep, 9, 285–289, 1986). More recently, the clinical use of GHB for ethyl alcohol anti-abstinence purposes has been described (see The Lancet, 2,787–789, 1989).

It has now surprisingly been found that γ-hydroxybutyric acid and physiologically equivalent forms can advantageously be utilised for the treatment of the so-called withdrawal syndrome from drugs, drugs of abuse, psychotropics, stupefacient and/or psychoactive substances and from nicotine; in particular, drugs such as narcotics, opiates, cocaine, cannabinoids or psychoactive substances such as benzodiazepines, psychostimulants, amphetamines, nicotine and their derivatives or the like. The use of γ-hydroxybutyric acid has also proved to be effective in the treatment of nutritional disorders such as bulimia, obesity and anorexia.

The withdrawal syndromes, dependences on drugs, drugs of abuse, psychotropics, stupefacient and/or psychoactive substances and nutritional disorders have as their common denominator the manifestation of so-called "craving" which can be defined as an intense and compulsive desire for a given substance or a given food.

γ-Hydroxybutyric acid has proved to be particularly active in inhibiting the onset of such-symptoms, as it has been possible to demonstrate on the basis of clinical experiments on 23 subjects meeting the diagnostic criteria of opiate dependence and on 3 patients affected by nutritional disorders (one case of anorexia, one of bulimia and one of obesity).

Table 1 shows the characteristics of the groups of subjects employed, in accordance with a "double blind" scheme, for the study of the activity of GHB in the treatment of the opiate withdrawal syndrome.

Eleven subjects were treated with GHB, including six who had used heroin in the last 24 hours (5 M, 1 F) and 5 undergoing methadone treatment (4 M, 1 F).

The control group consisted of 12 patients, 7 who used heroin (6 M, 1 F) and 5 undergoing therapy with methadone (3 M, 2 F). The two groups were homogeneous with regard to age, sex, duration and physical condition (Table 1).

TABLE 1

| Characteristics of the groups | GHB | PLACEBO |
|---|---|---|
| No. | 11 | 12 |
| M | 9 (81%) | 9 |
| Age (years) | 22 ± 2.3 | 21.6 ± 3 |
| Duration Tx (years) | 4 ± 1.5 | 3.5 ± 1.7 |
| Anti-HIV antibody positivity | 3 (27%) | 4 (33%) |
| Serious socioenvironmental problems | 6 (54%) | 8 (66%) |

In addition to the heroin abuse, the patients showed the simultaneous use of benzodiazepine and/or cocaine, cannabinoids, amphetamine-type psychostimulants or nicotine.

The GHB group was treated by the oral route in 6 administrations (1.5 mg/kg/weight/day).

The start of the treatment was decided on the basis of the onset of an abstinence symptomatology and was continued for 4 days in the case of the patients who had used heroin in the preceding 24 hours; treatment was continued for 8 days in the case of the patients who had used methadone.

If, within 1 hour, there was no manifestation of a regression of the symptomatology of the abstinence syndrome, the patient was referred for conventional anti-abstinence treatment.

On the 4th and 8th day respectively, the patients were subjected to a naltrexone induction by means of the administration of 0.4 mg of naloxone by the intravenous route, and then of 10 mg of naltrexone on the first day, 20 mg on the second day, 50 mg on the third and, then, were referred for a multimode treatment.

During hospitalisation, no provision was made for the intake of any other drug, other than those indicated.

The GHB treated subjects showed, at 15' from the first administration, a reduction in the symptomatology, which subsequently declined so as to disappear within 30'. The patients reported subjective wellbeing. In one case, a report was given of a feeling of slight dizziness, which disappeared after 30' without involving departure from the trial.

The absence of withdrawal symptoms and the feeling of wellbeing continued throughout the duration of the trial (Table 2).

In all the subjects, with the exception of one case, it was possible on the fourth day (heroin) or on the eighth day (methadone) to administer 0.4 mg of naloxone via the intravenous route and then 10 mg of naltrexone via the oral route, without the appearance of undesired effects.

The naltrexone induction was completed on the following days; subsequently, the patients were assigned to the out-patients multimode programme.

On completion of the trial, there was no evidence of the presence of drugs of abuse, psychotropics, stupefacient and/or psychoactive substances in the urine of any of the subjects of the GHB group.

No differences were noted in the results between the subjects who took heroin and those who were on methadone treatment.

TABLE 2

Abstinence from opiates, assessed according to the Wang scale, in subjects treated with GHB and with a placebo
(Scores from 0 to 10 - abstinence absent
from 10 to 20 - slight abstinence
from 20 to 30 - moderate abstinence)

|  | GHB | PLACEBO |
| --- | --- | --- |
| on intake | 10 (11–22) | 10 (11–21) |
| at 30' | 10 (3–5) | 10 (12–25) |
| at 3 hours | 10 (0–3) | 15 (15–26) |
| at 12 hours | 10 (0–3) | — |
| at 24 hours | 10 (0–5) | — |
| after naloxone | 10 (0–3) | — |

In the clinical study on 3 young female subjects affected by nutrition disorders and treated using the same dosage scheme but with doses 50% less than those utilised for the subjects affected by withdrawal syndromes, after one month from the start of the treatment a significant improvement was noted in the general clinical conditions and in the intensity of the craving.

The compositions forming the subject of the invention may be prepared by employing conventional excipients and techniques, such as those described in Remington's Pharmaceutical Sciences Handbook, Mack Pub. Co., New York, U.S.A.

The preferred administration route is the oral route using capsules, tablets, syrups or equivalent forms. It may be advantageous to employ administrations via the parenteral and/or intravenous route and delayed-release forms, for the purpose of reducing the frequency of administration imposed by the pharmacokinetics of the active principle.

The average daily dose will depend on a number of factors, such as the seriousness of the condition to be treated, as we 11 as the weight, sex and age of the patient but, in general, this dose will be within the range 0.5 to 10 mg/kg/day, preferably between 1 and 2.5 mg/kg/day.

We claim:

1. The method of treatment of a human subject affected by nutritional disorders which consists of administering to said human subject a composition containing 0.5–10 mgs/kg/day of body weight of said human subject of γ-hydroxybutyric acid, a salt thereof or the lactone thereof.

2. The method according to claim 1 wherein said composition contains 1–2.5 mgs/kg/day of γ-hydroxybutyric acid, a salt or the lactone thereof.

3. The method according to claim 1 wherein said composition is administered orally, parenterally or intravenously.

4. The method according to claim 1 wherein said nutritional disorder is bulimia or anorexia.

5. The method according to claim 3 wherein said composition is administered in the form of a delayed release formulation.

6. The method of treatment of a human subject affected by withdrawal symptoms from the use of a narcotic, an opiate, cocaine, benzodiazepine, a psychostimulant, amphetamine or nicotine or mixtures thereof which consists of administering to said human subject a composition containing 1.5 mg/kg/weight/day of γ-hydroxybutyric acid, a salt thereof or the lactone thereof.

7. The method according to claim 6 wherein said composition is administered orally, parenterally or intravenously.

8. The claim according to claim 7 wherein said composition is administered in the form of a delayed release formulation.

9. The method according to claim 6 wherein said human subject is affected by the simultaneous use of benzodiazepine, cocaine, heroin, an amphetamine-type psychostimulant and nicotine.

* * * * *